(12) United States Patent
Barata et al.

(10) Patent No.: US 8,012,263 B2
(45) Date of Patent: Sep. 6, 2011

(54) PROCESS FOR THE EVAPOCRYSTALLIZATION OF MALTITOL

(75) Inventors: Manuel Barata, Gonnehem (FR); Pierrick Duflot, La Couture (FR); Adem Gharsallaoui, Dijon (FR); Mohamed Mathlouthi, Coulommes-la-Montagne (FR)

(73) Assignee: Roquette Freres, Lestrem (FR)

( * ) Notice: Subject to any disclaimer, the term of this patent is extended or adjusted under 35 U.S.C. 154(b) by 172 days.

(21) Appl. No.: 12/260,343

(22) Filed: Oct. 29, 2008

(65) Prior Publication Data

US 2009/0114214 A1    May 7, 2009

(30) Foreign Application Priority Data

Oct. 30, 2007  (FR) ..................... 07 58704

(51) Int. Cl.
*C13B 30/02* (2006.01)

(52) U.S. Cl. ........................................ 127/60
(58) Field of Classification Search .................. None
See application file for complete search history.

(56) References Cited

U.S. PATENT DOCUMENTS

| | | | |
|---|---|---|---|
| 4,408,041 A | 10/1983 | Hirao et al. | |
| 4,846,139 A | 7/1989 | Devos et al. | |
| 5,773,604 A * | 6/1998 | Lefevre et al. | 536/104 |
| 2001/0006956 A1 | 7/2001 | Leleu et al. | |

FOREIGN PATENT DOCUMENTS

| | | | |
|---|---|---|---|
| EP | 0139573 | | 5/1985 |
| EP | 0189704 | | 8/1986 |
| EP | 0905138 | | 3/1999 |
| JP | 57-47680 | | 10/1982 |
| JP | 58158145 | | 9/1983 |
| WO | 0204473 | | 1/2002 |
| WO | WO02/04473 | * | 1/2002 |

OTHER PUBLICATIONS

Schouten A. et al.: "A redetermination of the crystal and molecular structure of maltitol (4-0-alpha-d-glucopyranosyl-d-glucitol)" Carbohydrate Research, Elsevier Scientific Publishing Company, Amsterdam, NL, vol. 322, No. 3-4, Dec. 12, 1999 pp. 298-302.
Search report dated Jul. 24, 2008 in French priority application.

* cited by examiner

*Primary Examiner* — Melvin Mayes
*Assistant Examiner* — Bijay Saha
(74) *Attorney, Agent, or Firm* — Young & Thompson

(57) ABSTRACT

A process for preparing maltitol crystals by evapocrystallization, includes preparing a maltitol solution with a maltitol richness of at least 85% based on dry matter, preferably a maltitol richness of between 89% and 99% based on dry matter, and even more preferably a maltitol richness of between 93% and 95% based on dry matter; concentrating under vacuum maltitol solution in the evapocrystallizer so as to obtain a maltitol syrup whose degree of maltitol supersaturation is within the metastable zone of maltitol; seeding the supersaturated maltitol solution with a maltitol seed crystal in dispersed form; performing the crystallization while keeping constant the degree of maltitol supersaturation within the metastable zone of maltitol by controlling the conditions of temperature, the conditions of vigorous stirring by pumping of the evaporation vapors, and the conditions of feeding in of the maltitol syrup to be crystallized; and recovering the crystals thus obtained.

17 Claims, No Drawings

PROCESS FOR THE EVAPOCRYSTALLIZATION OF MALTITOL

The invention relates to a process for crystallizing maltitol, characterized in that the crystallization is performed by evaporation under vacuum over a very short period of time.

The invention more particularly relates to a process that consists in evaporating a maltitol solution that is highly rich in maltitol, initially sub-saturated, so as to bring it to supersaturation within the metastable zone of maltitol at the temperature measured under partial vacuum.

Seeding is then performed with maltitol seed crystals whose size and dispersion in the supersaturated solution are controlled.

The invention consists then in keeping the maltitol supersaturation state constant throughout the entire period of growth of the crystals by controlling the conditions of temperature, conditions of stirring by pumping of vapors during evaporation, and conditions of feeding in of the maltitol syrup to be crystallized.

The invention thus allows for obtaining, in less than two hours, maltitol crystals of a perfectly controlled particle size distribution.

Maltitol (1,4-O-α-D-glucopyranosyl-D-glucitol) is a polyol obtained by hydrogenation of maltose.

The absence of a reducing end in the maltitol molecule confers a high thermal and chemical stability to maltitol.

Maltitol is lower in calories than sucrose, but has organoleptic properties similar to that sugar. It is non-cariogenic, and therefore is used in many food and pharmaceutical applications.

The only crystalline form of maltitol known to date is the anhydrous form, described in U.S. Pat. No. 4,408,041.

Indeed, it was not until 1983, the date of publication of said patent, that the company Hayashibara described for the first time the production of maltitol crystals.

Previously, this polyol had always been considered as an un-crystallizable product. In reality, this erroneous postulate arises from the fact that the crystallization of maltitol from a supersaturated solution is not as easy to control as in the case of other polyols, such as mannitol or erythritol. Moreover, maltitol solutions contained a large number of impurities constituted by polyols with a degree of polymerization greater than or equal to 3.

Certain characteristics intrinsic to maltitol, such as in particular its solubility, are also the cause of the observed difficulties.

For the purposes of the invention, the term "maltitol solubility" means the maltitol concentration of a saturated solution that is in equilibrium with maltitol in the solid state.

"Maltitol supersaturation" of a maltitol solution, at a given temperature, is defined for the purposes of the invention as the ratio of the mass of maltitol to the mass of water of the solution, relative to the mass of maltitol over the mass of water of the saturated solution in pure form.

The maltitol solubility curve and supersaturation limit curve (written as σ) as a function of temperature conventionally reflect the behaviour of maltitol in solution and divide the concentration domain as a function of temperature into three zones:

1) below saturation (σ<1) where crystallization is not possible,
2) between σ=1 and σ=1.08, the metastable zone where nucleation and growth may take place, and
3) above σ=1.08, the labile zone where spontaneous nucleation, growth and amorphization may take place in an uncontrolled manner.

The metastable zone of a given compound is conventionally characterized by spontaneous generation of seed crystals that may grow or disappear, the seeds thus formed being non-uniform and of irregular geometry.

For maltitol, the supersaturation limit of the metastable zone is σ=1.08 (Schouten et al. 1999, *Carbohydrate Research*, 322, 298-302). This value is relatively low when compared with that of other sugars, and makes the control of crystallization particularly tricky.

The solubility of maltitol in water is of critical importance for determination of the supersaturation, which represents the driving force governing the crystals growth.

Among all the factors liable to have an influence on the solubility of maltitol in water, the temperature is considered as being the factor having the most pronounced effect (Ohno and Hirao, 1982, *Carbohydrate Research*, 108, 163-171).

The solubility of maltitol effectively increases significantly as the temperature increases. As an indication, the solubility rises from 132.5 g per 100 ml of water at 8.5° C. to 567.3 g per 100 ml of water at 90° C. (article by A. GHARSALLAOUI et al. awaiting publication in *Food Biophysics*).

So far, the use of these basic rules in maltitol crystallization processes described in the prior art has only led to mixed results.

The reason for this is that crystallization is a complex operation involving many factors that are not always known and controlled.

It should also be mentioned that the final shape of a crystal highly depends on crystallization conditions. Impurities may also modify the shape (or habitus) of a crystal, such as a prismatic and bipyramidal forms of a maltitol crystal in the presence of different concentrations of maltotriitol, as described by the Applicant Company in its patent EP 905 138.

Impurities also have many other effects on crystallization, up to the point of completely preventing it.

Moreover, if crystallization is not controlled, an amorphous product whose structure may evolve towards a more stable state may even be obtained. This "glass transition" depends on the structure and on environmental conditions of temperature and humidity.

In general, crystallization is considered as a physical process that systematically involves two basic mechanisms: nucleation and crystal growth.

The two phenomena take place in the supersaturated solution, and, with regard to the mode for obtaining the supersaturated solution, various crystallization modes are distinguished: thermal processes in which supersaturation is achieved by cooling, evaporation or a combination of the two, and processes involving addition of a cosolvent or of an additive that modifies the properties of the system.

When the solubility of the compound to be crystallized increases rapidly with temperature, cooling may constitute the appropriate process for crystallization, and, in fact, it is often the most frequently process used.

The solution is cooled to a certain level of supersaturation. Creation of interfaces (or crystal seeds) may be obtained by sudden or slow cooling or, in the majority of cases, by seeding.

In fact, the choice depends on the nature of the solute and of the crystals desired.

Enlargement of crystals is generally performed by gradually reducing the temperature. In this type of process, the temperature profile is therefore the critical controlling factor. The temperature difference between the mass in the process of being crystallized and the cooling fluid should not be too high, to avoid the risk of crystal formation on the metal surface of the heat exchanger used for the cooling operation, a solid deposit process known as a "crust" or "lining", which creates an additional resistance to the transfer.

Industrially, crystallization by cooling of maltitol is not limited by the rate of crystal growth, but by the cooling capacity of the solution submitted to crystallization.

In the case of maltitol, the phase of crystallization by cooling is thus often preceded by a step of concentration by evaporation, which allows for obtaining and then maintaining supersaturation.

It thus appears that an acceptable yield cannot be obtained in a single step, without entailing the risk of obtaining a product of reduced purity.

In the case of maltitol, the process is generally performed in several steps, the mother liquor derived from the first crystallization, after separation of the crystals, serving to feed a new crystallization.

An alternative to this step of crystallization by depletion may be the treatment of the mother liquor by chromatography, generally in a simulated mobile bed.

A combination of an evaporation step and a cooling step may also be performed, by introducing the hot solution into a chamber at reduced pressure.

This results in spontaneous ("flash") vaporization, the gradual reduction in pressure making it possible to maintain supersaturation. Starting from a certain supersaturation value, the cooling operation is performed.

The first commercialized semicrystalline maltitol powders were prepared via a "bulk solution" technique, consisting in setting to a solid a dehydrated maltitol solution exhibiting a richness that may at best be up to 90%, by adding a seed composed of sugar or polyol crystals. Such a process is described, for example, in patents JP 57-47680 and JP 58-158145.

It has also been proposed in U.S. Pat. No. 4,408,401 to prepare pulverulent crystalline mixtures, known as "total sugar", by atomization of precrystallized solutions or massecuites. These are obtained by very slow cooling of a supersaturated aqueous maltitol solution containing in addition large amounts of polyols such as sorbitol, maltotriitol, maltotetraitol and other polyols with a higher degree of polymerization.

This very slow cooling, and this addition of a maltitol seed crystal, are in effect necessary in this process for the formation and growth of the maltitol crystals.

However, this "total sugar" is far from being sufficiently crystalline, since it also needs to be further dried, for about 40 minutes, and also to be matured for ten hours.

However, its stability to water vapor is mediocre, and it is often criticized for setting to a solid on storage.

The Applicant Company has contributed, in its patents EP 185 595 and EP 189 704, towards providing a first solution to these difficulties by proposing the preparation of crystalline maltitol powders of very high richness, using processes based on fractionation techniques via continuous chromatography.

These processes make it possible to obtain, at a competitive cost, powders with a purity of greater than 99%, through crystallization in aqueous solution of the maltitol present in the chromatographic fraction particularly rich in this polyol.

The techniques known as "bulk solution", on the one hand, and of crystallization in aqueous solution, on the other hand, have long been considered as the only processes used industrially for producing crystalline maltitol.

However, industrially, the most difficult step to master remains the control of the size and shape of the crystals.

Specifically, the crystallization of maltitol generates dust by attrition in large-capacity crystallizers, by cooling or during drying.

The presence of fine crystals, the inhomogeneity of the particle size and the natural hygroscopic tendency of maltitol led specialists in the field of crystallization of polyols to search for a crystallization method capable of ensuring prolonged stability with respect to water vapor and temperature under the conditions usually used in storage, transportation and conditioning of crystalline maltitol powder.

Alongside the techniques of "bulk solution" and of crystallization by cooling in aqueous solution, evaporation crystallization processes were then studied.

However, most of these studies directed towards crystallization of maltitol used excessively long conventional processes, combining evaporation and cooling.

Specifically, it was often a matter of ensuring the maturation of crystals in a bulk solution, which were collected and then dried and ground without taking mechanical consequences into account, such as breaking of crystals, formation of dust and increase of hygroscopicity.

Examples that may be mentioned include:

patent application US 2006/0 078 662, which teaches the manufacture of maltitol without seeding. The solution is first concentrated by evaporation to a residual humidity of 4.5% to 6%, and then cooled to a temperature of 10 to 20° C. The concentrated and cooled solution is finally fed into an extruder.

The product obtained after grinding has an excessively dispersed particle size, between 50 and 500 μm, with a residual humidity of 0.2% to 0.8%, characteristic of an unstable product, and a melting point of between 144 and 148° C., characteristic of a product of low purity (the melting point of pure maltitol being between 146 and 147° C.).

International patent application WO 2005/014 608 describes the preparation of a maltose-rich syrup (70% to 80% on a dry weight basis) enriched by chromatographic separation (maltose content of more than 92% on a dry weight basis) and then catalytically hydrogenated before concentration and then solidification or crystallization and drying. The maltitol crystal has a solids content of 98.5% for a maltitol richness of greater than or equal to 97%.

However, when this crystallization is used to purify the maltitol solution after chromatography, it is mostly by way of numerous long, complicated and laborious steps.

Patent application EP 139 573 describes a surface "flash" evaporation and continuous recycling of the maltitol solution, which is heated outside the evaporator in a heat exchanger using the heat of the compressed vapor.

A portion of the solution is collected along with the crystals to separate said crystals from the mother liquors, which are then recycled. The crystals are collected in part by decantation in a stem of the crystallizer.

However, this method involves many individual operations (flash evaporation, vapor compression, heat exchange, decantation), which do not make it particularly attractive or industrially viable.

Finally, international patent application WO 02/04473 encompasses the preparation of maltitol crystals via an evapocrystallization process performed under laboratory conditions, modelled on crystallization processes conventionally used in the sugar industry.

This method consists essentially in an evapocrystallization performed with impurities added to a hydrogenated maltose syrup containing a broad spectrum of residual oligomers.

Patent application WO 02/4473 describes the production of crystalline maltitol with a yield of 50% to 80% maltitol and 60% to 70% solids. These yields are obtained after evapocrystallization, using the difference in solids between the mother liquors and the crystals.

Such concentrations of solids cannot be transposed to industrial conditions, given the difficulties that they would generate in steps such as the pumping and centrifugation steps.

Moreover, crystallization by evaporation is not used alone; it is necessary to combine it with a cooling step.

In point of fact, only the crystallization initiator is prepared by evaporation, the crystallization itself being performed conventionally by cooling for 30 hours.

It is mostly found that supersaturations performed are too high to be able to efficiently control the size or shape of the crystals obtained.

Indeed, it should be reminded that the limit of the metastable zone of maltitol is σ=1.08, and that the supersaturations mentioned in patent application WO 02/4473 are within the labile zone, which, by definition, is uncontrollable.

Finally, the poorly defined yields relate more to the mass of maltitol cream retained in the centrifuge than to a true yield of crystals.

From the foregoing, it results that there is an unsatisfied need for a maltitol crystallization process allowing for the control of the size and shape of maltitol crystals, without having to perform long, laborious, difficult and complex steps.

The Applicant Company has, to its credit, reconciled all these objectives, which were until now considered difficult to reconcile, by proposing a remarkably fast maltitol evapocrystallization process, which is based on the control of the quality of crystallization seeds and of the conditions of maltitol solubility and maltitol solution supersaturation the throughout crystals growth.

The present invention thus relates to a process for preparing maltitol crystals by evapocrystallization, characterized in that it consists in:

a) preparing a maltitol solution with a maltitol richness of at least 85% based on dry matter, preferably a maltitol richness of between 89% and 99% based on dry matter, and more preferentially a maltitol richness of between 93% and 95% based on dry matter, b) concentrating said maltitol solution under vacuum in an evapocrystallizer so as to obtain a maltitol syrup whose degree of maltitol supersaturation is within the metastable zone of maltitol, c) seeding the supersaturated maltitol solution with a maltitol seed crystal in dispersed form, d) performing the crystallization while keeping constant the degree of maltitol supersaturation within the metastable zone of maltitol by controlling conditions of temperature, conditions of vigorous stirring by pumping evaporation vapors, and conditions of feeding in of the maltitol syrup to be crystallized, e) recovering the crystals thus obtained.

The process of crystallization by evaporation according to the invention consists in evaporating the maltitol solution to the point of supersaturation, and then seeding and maintaining a constant degree of supersaturation in order to achieve enlargement of the seed crystals.

The first step consists in preparing a maltitol solution with a maltitol richness of at least 85% based on dry matter, preferably with a maltitol richness of between 89% and 99% based on dry matter, and even more preferably with a maltitol richness of between 93% and 95% based on dry matter.

In the present invention, the notion of richness should be understood as corresponding to the percentage of maltitol expressed as dry weight/dry weight relative to all the carbohydrates present in the crystalline maltitol composition.

These carbohydrates may be polyols such as, in particular, sorbitol, polyols with a degree of polymerization (or DP) of 3 and polyols with a DP of 4. This richness is usually measured by high-performance liquid chromatography.

The preparation of the maltitol solution may be performed via any method known to those skilled in the art.

It is, for example, possible to follow the teaching of patent EP 905 138, of which the Applicant Company is the proprietor, by controlling the steps of the processes described so that the maltitol syrup contains a maltitol richness of at least 85% based on dry matter, preferably a maltitol richness of between 89% and 99% based on dry matter, and even more preferably a maltitol richness of between 93% and 95% based on dry matter, and a maltotriitol content of less than or equal to 1% based on dry matter, and preferably less than or equal to 0.5% based on dry matter.

The second step of the process in accordance with the invention consists in concentrating under vacuum the maltitol solution thus prepared so as to obtain a maltitol syrup whose degree of maltitol supersaturation is within the metastable zone of maltitol.

The concentrating of the maltitol solution is performed by evaporating water from said solution, this evaporation being performed by supplying saturated vapor via a heat exchanger placed either in the evapocrystallizer or in a recycling loop.

To create supersaturation of the maltitol solution thus obtained, the solution must be modified such that the maltitol concentration exceeds its solubility and thus leads to an initial syrup having a supersaturation of between 1.04 and 1.08, located in the metastable zone of maltitol.

The Applicant Company has determined that these supersaturation values were achieved, for a maltitol solution with a richness of between 93% and 95%, at a cooking temperature of between 75 and 85° C. and under a partial vacuum of between 20 and 30 kPa.

As will be illustrated hereinafter, if the nominal value is set at 22 kPa, this corresponds to a cooking temperature of 76° C.

The amount of water to be evaporated off is determined by calculation, from the initial maltitol concentration.

The third step of the process in accordance with the invention consists, after having achieved a supersaturation value of between 1.04 and 1.08, for example a value of 1.05 or of 1.07, in seeding the supersaturated maltitol solution with a maltitol seed crystal in dispersed form.

This seeding is performed with maltitol crystals having a mean size, measured by laser granulometry, of between 10 and 50 μm, preferably between 20 and 30 μm and more preferably of about 25 μm.

These sizes are determined on a laser scattering granulometer of LS 230 type from Beckman-Coulter, equipped with a powder dispersion module (dry route), according to the manufacturer's technical manual and specifications.

The measuring range of the LS 230 laser scattering granulometer is from 0.04 μm to 2000 μm.

The operating conditions of screw speed under the hopper and of intensity of vibration of the dispersion chute are determined such that the optical concentration is between 4% and 12%, ideally 8%.

The results are calculated as volume percentages, and expressed in μm.

The maltitol crystals used as seeds are dispersed in a saturated maltitol solution, or in polyethylene glycol, especially PEG-300, a food-grade solvent having a relatively high viscosity allowing the dispersion and separation of the crystals, which are generally agglomerated due to their small size.

The dispersion of the crystallization seeds, by virtue of the partial vacuum and the high temperature, makes it possible to minimize the agglomeration and the formation of twins.

The amount of seeds introduced is calculated as a function of the theoretical size of the crystals to be obtained according to the following formula (f) (from ROGE and MATHLOUTHI, in AVH Association, 12th Symposium—Reims, March 2005):

$$\frac{m_c}{m_s} = \left(\frac{L_c}{L_s}\right)^3$$

in which:
$m_c$: mass of crystals to be obtained;
$m_s$: mass of seed crystals;
$L_c$: mean size of the crystals after crystallization;
$L_s$: size of the seed crystals,
(according to B. ROGE et al., AVH Association—12th Symposium—Reims, March 2005, pp. 15-22).

The fourth step of the process according to the invention then consists in performing crystallization while keeping constant the degree of maltitol supersaturation within the metastable zone of maltitol by controlling the conditions of temperature, conditions of vigorous stirring by pumping of the evaporation vapors, and conditions of feeding in of the maltitol syrup to be crystallized.

After introducing the crystallization seeds, which is performed while taking care not to introduce air into the massecuite (since air modifies vacuum, cooking temperature and also supersaturation of the medium, any spontaneous nucleation should be avoided), the growth phase of the crystals is performed under a partial vacuum kept constant.

The evaporation is performed such that a vigorous and well-controlled stirring of the supersaturated maltitol solution is obtained in the evapocrystallizer.

The water that evaporates from said solution in fact creates a pumping phenomenon that stirs the solution vigorously.

This phenomenon makes it possible to stir the solution with an amplitude much greater than that which would be generated by mechanical stirring.

The evaporated water is then either removed from the evapocrystallizer, or condensed inside the evapocrystallizer.

The dry matter of the solution entering the evapocrystallizer is also adjusted so as to obtain the amount of saturated vapor that is necessary and sufficient for pumping.

Moreover, it should be noted that the vigorous stirring induced by control of the evaporation allows homogeneity of the heat and matter transfers, which results, as will be demonstrated, in a controlled growth of the crystals and a reduction in spontaneous nucleation that generates fine grains, which are the cause of the problems of setting to a solid generally observed in the prior art.

The Applicant Company moreover recommends performing this fourth step of the process according to the invention in successive stages, each stage being constituted either:
of a concentration phase by external evaporation, and then
of a "condensation" resting phase (internal evaporation), at
a constant overall concentration,
as will be illustrated hereinbelow.

The phases of concentration by evaporation of the massecuite are known as "massecuite cooking". They make it possible to compensate for the reduction in supersaturation of the maltitol mother liquor induced by crystal growth.

The evapocrystallization is performed for a total time of less than 2 hours, preferably between 30 and 90 minutes and even more preferably between 40 and 70 minutes.

To the Applicant Company's knowledge, no process for crystallizing maltitol so quickly has ever been described in the prior art. The crystallization time is thus from 10 to 40 times shorter than the time required for crystallization by cooling.

The cooking temperature is kept constant at between 70 and 85° C. and preferably between 72 and 80° C.

The fifth and final step of the process in accordance with the invention consists in recovering the crystalline maltitol.

Washing of the crystals is performed via any method known to those skilled in the art.

The crystals obtained are analyzed in terms of shape, size and particle size distribution.

The crystal habitus is determined by both optical and electron microscopy.

In optical microscopy, the crystals are placed in a glass crucible and examined under Nikon binoculars equipped with an objective lens having a maximum magnification of 250. A camera is connected to a computer-based image acquisition system.

Images are acquired on 256 levels of grey, and have a resolution of 752×548 pixels. The sample is illuminated with optical fibres providing a cold light, which is favorable for maintaining the sample in its initial state.

In electron microscopy, observations are performed using a Quanta 200 FEG FEI scanning electron microscope.

Crystals are observed under a voltage of 2 to 5 kV. The photographs are taken under the microscope with a magnification of 50 to 350 times and then enlarged during printing.

The crystals obtained by crystallization of a maltitol solution containing less than 1% maltotriitol have a bipyramidal shape, as taught by the Applicant Company in its patent EP 905 138.

The size of the crystals, determined with a laser granulometer, is between 50 and 550 µm, preferably between 150 and 400 µm and more preferably between 150 and 350 µm.

The Applicant Company has surprisingly found that the particle size distribution of the maltitol crystals obtained is of Gaussian type, with a coefficient of variation not exceeding 60% and preferably not exceeding a value of between 45% and 55%.

It should also be noted that the evapocrystallization process according to the invention, applied to 93% maltitol solutions containing about 0.5% maltotriitol, rapidly leads to crystals of bipyramidal shape whose very narrow particle size distribution makes it possible to obtain a fluid maltitol powder of excellent flowability, which does not set to a solid under storage conditions varying within very wide temperature range (from 15 to 30° C.) and relative humidity range (45% to 75%).

Finally, the crystallization yield is relatively high, between 55% and 65%, expressed as dry weight of the crystals recovered from the massecuite relative to the dry weight of the said massecuite.

The invention will be understood more clearly by reading the example that follows, which is given for illustrative and non-limiting purposes.

EXAMPLE

The crystallization consists in evaporating a maltitol solution until it reaches a maltitol concentration within the limits of the metastable zone, and then in seeding and maintaining supersaturation within said limits in order to achieve enlargement of the seed crystals.

The crystallization is performed in an industrial evapocrystallizer equipped with an agitator positioned in a central well, constituted of a container with a volume of 6 m$^3$. A cylindrical tubular heat exchanger is fed with saturated water vapor. The vapor is provided by means of a boiler at a pressure of 1 bar (100 kPa). The cooking temperature is continuously controlled.

The partial vacuum is obtained using a liquid-ring pump equipped with a membrane pressure switch. The nominal pressure is maintained at 22 kPa, which corresponds to a vapor temperature of between 72 and 74° C. and a cooking temperature of 76° C.

The cooking of the massecuite is performed by outward evaporation of the vapors, until the supersaturation solids content is reached.

Phases of water evaporation and phases of internal water condensation are then alternated so as to control supersaturation and in particular the vigorous stirring by pumping of the vapors during crystallization.

Additional live saturated vapor is fed in if necessary, to maintain stirring of the massecuite.

The temperature at the end of cooking is 80° C.

Graining is performed by introducing into the bulk solution calibrated maltitol crystals (of about 25 µm) dispersed in PEG-300, in an amount sufficient to prevent decantation of the seeds.

Crystallization is performed under a partial vacuum (22 kPa) and comprises:
concentration of the solution by evaporation so as to obtain a supersaturation equal to 1.07. The amount of water to be evaporated off is determined by calculation, from the initial concentration.
when the desired supersaturation is reached, seeding by introducing an amount of calibrated seeds, the amount being calculated according to the formula (f) given hereinabove.

The period that follows this graining is composed of several evaporation phases interspersed with rest periods, as indicated in the tables below.

The crystallization in stages lasts for 54 minutes, and the temperature is between 76 and 80° C. Recovery of the crystals is then performed. Two consecutive washes with water allow recovery of a powder of dry and fluid crystals after centrifugation and drying of the crystals.

TABLE I

| composition of the maltitol solution to be crystallized and crystallization conditions | |
|---|---|
| Mass of the maltitol solution | 2000 kg |
| Concentration of the maltitol syrup | 58% |
| Maltitol richness | 93% based on solids |
| Maltotriitol content | 0.5% based on solids |
| Duration of the initial concentration step | 18 minutes |
| Solids content at the temperature of seeding | 80% |
| Mass of seeds | 500 g in PEG-300 |
| Seeding temperature | 76° C. |
| Mean seed size | 25 µm |
| Seeding supersaturation | 1.07 |
| Pressure | 22 kPa |
| Number of evaporation stages | 3 |
| Number of internal condensation stages | 3 |
| Total duration of the stages | 54 minutes |
| Mass of water evaporated off | 700 kg |
| Mass of water condensed | 875 kg |
| Amount of vapor pumping | ~10 000 m$^3$/h |

TABLE I-continued

| composition of the maltitol solution to be crystallized and crystallization conditions | |
|---|---|
| Amount of pumping of the mechanical stirrer | ~2000 m$^3$/h |
| Temperature at the end of crystallization | 80° C. |

TABLE II

| details of the evaporation stages | |
|---|---|
| Successive stages of | Test 1 |
| Evaporation/condensation | 10 minutes |
| Condensation | 5 minutes |
| Evaporation/condensation | 8 minutes |
| Condensation | 10 minutes |
| Evaporation/condensation | 6 minutes |
| Condensation | 15 minutes |

The condensation stages make it possible to overcome the slowing-down of the crystallization rate that usually accompanies the decrease in maltitol richness of the solution during crystallization.

TABLE III

| characterization of the crystals obtained | |
|---|---|
| | Test 1 |
| Mass of crystals obtained in the evapocrystallizer | 600 kg |
| Yield | 51.7% solids |
| Mean size | 300 µm |
| Particle size distribution (coefficient of variation) | 52% |
| Shape of the crystals | Bipyramidal |

The evaporation under vacuum via the process in accordance with the invention makes it possible to considerably lower the crystallization time compared to the conventional cooling process, and to obtain bipyramidal crystals of uniform size and of narrow particle size distribution.

The invention claimed is:

1. Process for preparing maltitol crystals by evapocrystallization, wherein the process comprises:
   a) preparing a maltitol solution with a maltitol richness of at least 85% based on dry matter,
   b) concentrating said maltitol solution under vacuum in an evapocrystallizer so as to obtain a maltitol syrup whose degree of maltitol supersaturation is within the metastable zone of maltitol,
   c) seeding the maltitol syrup with a maltitol seed crystal in dispersed form,
   d) performing the evapocrystallization while keeping constant the degree of maltitol supersaturation within the metastable zone of maltitol by controlling the conditions of temperature, conditions of vigorous stirring by pumping evaporation vapors, and conditions of feeding in of the maltitol syrup to be crystallized, and
   e) recovering crystals thus obtained.

2. The process according to claim 1, wherein the maltitol solution has a maltitol richness of between 89% and 99% based on dry matter.

3. The process according to claim 2, wherein the maltitol solution has a maltitol richness of between 93% and 95% based on dry matter.

4. The process according to claim 1, wherein the evapocrystallization is performed at a cooking temperature of between 75 and 85° C. and at a pressure of between 20 and 30 kPa.

5. The process according to claim 1, wherein the seeding is performed with crystals between 10 and 50 μm in size.

6. The process according to claim 5, wherein the seeding is performed with crystals between 20 and 30 μm in size.

7. The process according to claim 6, wherein the seeding is performed with crystals of about 25 μm in size.

8. The process according to claim 1, wherein the maltitol seed crystals are dispersed in a food-grade solvent of relatively high viscosity chosen from the group consisting of saturated maltitol syrup and polyethylene glycol so as to prevent the formation of aggregates or twins.

9. The process according to claim 8, wherein the food-grade solvent of relatively high viscosity is PEG-300.

10. The process according to claim 1, wherein the evapocrystallization is performed by stages of evaporation/condensation and of condensation for a duration of less than 2 hours.

11. The process according to claim 10, wherein the evapocrystallization is performed by stages of evaporation/condensation and of condensation for a duration of between 30 and 90 minutes.

12. The process according to claim 11, wherein the evapocrystallization is performed by stages of evaporation/condensation and of condensation for a duration of between 40 and 70 minutes.

13. The process according to claim 1, wherein the maltitol crystals obtained have a particle size of between 50 and 550 μm.

14. The process according to claim 13, wherein the maltitol crystals obtained have a particle size of 150 and 400 μm.

15. The process according to claim 14, wherein the maltitol crystals obtained have a particle size between 150 and 350 μm.

16. The process according to claim 13, wherein the maltitol crystals obtained have a particle size distribution of Gaussian type with a coefficient of variation not exceeding 60%.

17. The process according to claim 16, wherein the coefficient of variation does not exceed a value of between 45% and 55%.

* * * * *